United States Patent [19]

Wutzler et al.

[11] Patent Number: 5,008,079
[45] Date of Patent: Apr. 16, 1991

[54] APPARATUS AND METHOD FOR STERILIZING OR DISINFECTING OBJECTS

[75] Inventors: Peter Wutzler; Horst Mücke, both of Erfurt, German Democratic Rep.; Lauri Santasalo, Helsinki, Finland

[73] Assignee: OY Santasalo-Sohlberg AB, Finland

[21] Appl. No.: 299,968

[22] Filed: Jan. 19, 1989

[30] Foreign Application Priority Data

Jan. 19, 1988 [FI] Finland .................................. 880221

[51] Int. Cl.$^5$ .............................................. A61L 2/18
[52] U.S. Cl. ...................................... 422/28; 422/295
[58] Field of Search ................................ 422/28, 295

[56] References Cited

U.S. PATENT DOCUMENTS 4,129,517 12/1978 Eggensperger et al. ............ 514/714
4,909,988 3/1990 Childers et al. ....................... 422/26

FOREIGN PATENT DOCUMENTS 0109352 11/1987 European Pat. Off. .

Primary Examiner—Robert J. Warden
Assistant Examiner—Jill Johnston
Attorney, Agent, or Firm—Steinberg & Raskin

[57] ABSTRACT

Method and apparatus for sterilizing or disinfecting objects, especially thermosensitive objects, in a closed chamber such as an autoclave. The use of such sterilizing or disinfecting takes place particularly in health institutions such as hospitals, outpatient departments, etc., as well as in the pharmaceutical industry. The sterilization or disinfection is carried in a strong oxidizing agent, which can be an organic peracid, advantageously peracetic acid in gaseous form. Sterilization or disinfection is carried out in a closed chamber, under a vacuum or at atmospheric pressure. Utilizing a vacuum increases concentration of the active agent in the chamber, so that the requisite sterilizing time is shortened. According to the procedure, the sterilization or disinfection is carried out at, e.g. 40° to 50° C. which also increases the concentration of the active agent, so that a short action time is achieved involving minimal thermal stress on the objects which are being sterilized or disinfected. The peracetic acid used in the method is completely environmentally protective and safe because it disintegrates rapidly into oxygen and harmless acetic acids.

13 Claims, 1 Drawing Sheet

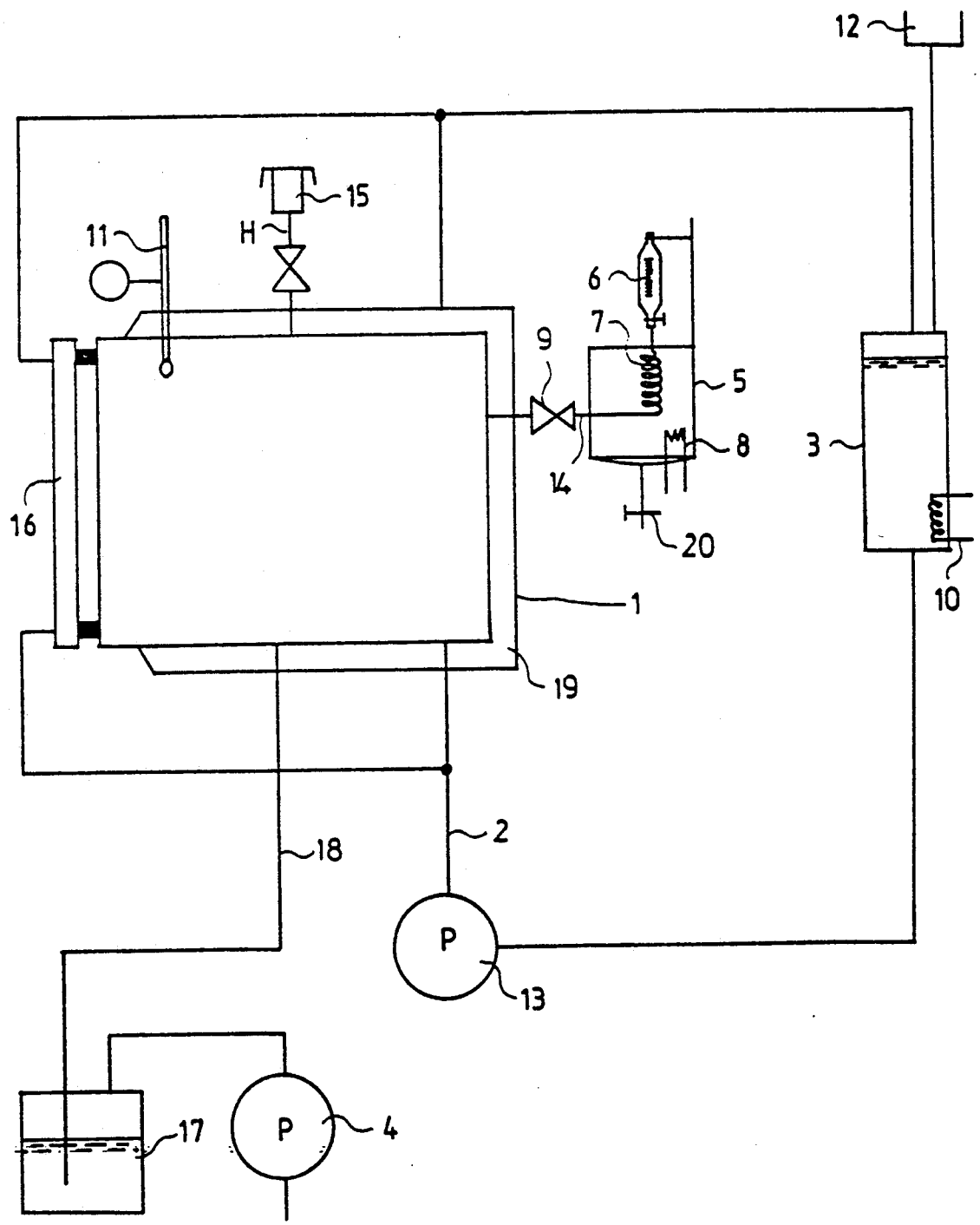

APPARATUS AND METHOD FOR STERILIZING OR DISINFECTING OBJECTS

BACKGROUND OF THE INVENTION

The present invention concerns a procedure and means for sterilizing or disinfecting instruments, in particular thermosensitive instruments in a vacuum chamber, advantageously in an autoclave, in which sterilization or disinfection is performed with a powerful oxidizing agent which is an organic peracid.

The use takes place particularly in institutions related to health such as hospitals, out-patient departments, etc., as well as in the pharmaceutical industry.

A plurality of methods are in use in hospitals, etc., for sterilizing thermosensitive objects, the most important of these being use of ethylene oxide, formaldehyde gas, glutaridialdehyde, $\beta$-propiolactone, and irradiation sterilization.

However, procedures currently in use involve several practical problems and drawbacks.

Ethylene oxide is a very toxic substance. It is carcinogenic, penetrates deeply into most materials and adheres to them strongly. Therefore, objects to be sterilized are required to be ventilated for a long period of time, for one day and night and even up to several months. In order to render ethylene oxide safer, it is mixed with Freon gas, however this gas ends up in the atmosphere and thereby leads to disintegration of the ozone layer. Ethylene oxide is also used in pure form. However, in this state it is an easily flammable and explosive substance.

Recently, formaldehyde has also been frequently used. This substance is extremely toxic and causes allergies. Additionally, it has an odor which adheres to the goods being sterilized, and also remains therein. The ventilation time is about twenty-four hours.

Additionally, a commonly used glutaric aldehyde may be noted. It is used in liquid form and another sterilizing substance needs to be used to activate the same. The subsequent flushing and drying of objects endangers sterilization. Therefore, sterilization is no longer discussed in this context; the term antiseptic preparation is used instead.

One more substance that has been used is $\beta$-propiolactone. Disadvantages related to this substance are, for instance, that it is extremely dangerous and has an extremely powerful carcinogenic effect.

Irradiation sterilization cannot be accomplished in small or minor units, since it requires comprehensive and expensive installations and extensive protective measures. Generally, irradiation sterilization per target is allowed to be carried out only once.

In European Patent No. 0,109,352, a procedure for sterilizing thermosensitive objects is presented using 4 to 7% peracetic acid as a sterilizing substance, in which objects to be sterilized are sterilized when packed in a chamber which is at 10 to 100 mbar pressure. A drawback also of this procedure is impracticality in certain respects, specifically concerning the relatively long sterilizing time, while the dilution of the treatment preparation in water is disadvantageous in the procedure of European Patent No. 0,109,352 for two reasons. Firstly, the moisture concentration (mg per liter) to be achieved is again reduced, which is decisive in view of the effect. Secondly, as a result of the higher temperature, hydrolytic transformation of the peracetic acid into acetic acid and hydrogen peroxide takes place.

No agent or method without these accompanying drawbacks has been tried before. It is therefore to be noted that no agent without any danger is available for rapid sterilizing or thermosensitive objects.

SUMMARY OF THE INVENTION

Accordingly, it is an object of the present invention to provide a procedure and apparatus for developing and accomplishing safe sterilization or disinfection of thermosensitive objects in an economical and environmentally protective manner, as well as rapidly, so that the drawbacks presented above can be avoided.

It is also an object of the present invention to sterilize or disinfect goods which are situated, in a manner known per se, in a packaging for preserving sterility, of which bags closed by binding are especially suitable, by utilizing environmentally protective gases so that when a package is taken for sterilization, the sterilizing is preserved after the package is removed out of the sterilizing means or apparatus.

These and other objects are attained by the present invention which is directed to a method for sterilizing o disinfecting instruments in a closed chamber, comprising carrying out the disinfecting or sterilizing with an organic peracid in a concentration of more than about 7 and up to about 50% in aqueous solution, this organic peracid being a powerful oxidizing agent. The sterilizing or disinfecting is preferably carried out in an autoclave, with thermosensitive instruments being disinfected or sterilized.

The present invention is also directed to apparatus for sterilizing or disinfecting instruments, which comprises a closable chamber, a jacket surrounding the closable chamber, and a vaporizer communicating with an interior of the chamber through a line fitted with a valve. Alternatively, an electrical resistance surrounding the closable chamber may replace the jacket. Furthermore, the apparatus for sterilizing or disinfecting instruments may comprise a closable chamber, means for heating the closable chamber which is disposed on an outside thereof, and means for vaporizing the sterilizing or disinfecting agent which include a heating element spiral or a cup/bowl-like depression located within the chamber itself.

Accordingly, the objects of the present invention are achieved by the concentration of the aqueous solution of peracetic acid used being more than about 7 and up to about 50%.

Useful acids in the procedure of the present invention include, for instance, performic acid, halogenated peracetic acids, perpropionic acid, halogenated perpropionic acids, perbutane acid and halogen derivatives thereof, perisovaleric acid and halogen derivatives thereof, percapronic acid and halogen derivatives thereof, percrotonic acid, monosuccinic acid, monoperglutaric acid, perbenzoic acid, and peracetic acid.

Contrary to the procedures of the prior art, even about a 20 to 50% organic peracid solution can be used with the present invention, with the concentration of the aqueous solution of the peracid used being advantageously about 40%, meaning that with the present invention a short sterilizing time, i.e. 60 minutes, is required which remarkably increases the usefulness of the present invention herein. The versatility of the present invention is also thereby increased in that, if necessary, the method can be carried out at room temperature, no vacuum needs to be established within the interior of the chamber, and objects to be sterilized may be taken into the chamber in packed or unpacked form.

Additionally, the means of the present invention are characterized by comprising a closed chamber surrounded by a jacket thermostatically-controlled, a vaporizer communicating with the chamber through a line which is closable with a valve, as well as possibly a vacuum pump which communicates through a line with the interior of the chamber, along with a separately-disposed heating vessel by which a water circulation system communicates with the jacket itself.

In the means of the present invention, a sterilizing or disinfecting agent need no longer be mixed separately in water, but can be introduced or dosed directly into the means itself.

Although the following description refers to sterilization, the present invention can also be used for disinfection.

Peracetic acid, which in view of the invention is the most preferred because of its properties and environmentally protective quality, disintegrates according to the following reaction equation:

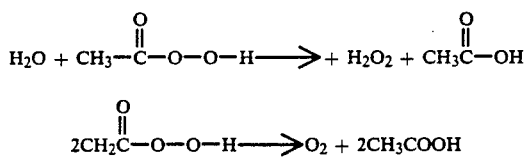

into oxygen and harmless acetic acid. The agent exercises a very efficient influence against all micro-organisms (bacteria, fungi, viruses, germs).

The means of the present invention comprise a closed chamber in which sterilization is performed. The chamber is surrounded by a hot water jacket controllable by a thermostat, its purpose being the heating of the interior of the chamber. The heating can also be carried out with the aid of an electrical resistance connected to the chamber itself.

A separately arranged heating vessel provided with a heating element is connected to the hot water jacket by a pump and a water circulation system. Wetting means communicate with the interior of the chamber by a line which is closable with a valve. For moistening the agent, a spiral or bowl-like depression has been provided in the wetting means. Both the spiral and bowl-like depression may also be disposed directly in the chamber itself.

A vacuum pump preferably communicates with the interior of the chamber.

A draining tap for moisture residue is preferably provided at a lowest point of the bowl-like depression.

Sterilizing is carried out in a closed chamber, in particular in an autoclave, from which air can be removed with the aid of a vacuum pump. When sterilizing takes place in a vacuum, the sterilizing time can be remarkably shortened by raising the concentration of the active agent in the chamber. Sterilizing in a vacuum may also be carried out so that subsequent to establishing the vacuum, part of the dosed or introduced sterilizing agent is removed, after which it is added again if need be. This also facilitates the increase of the concentration of the active agent and spreading of the agent within the chamber.

Sterilizing agent is conducted into the chamber in which the objects to be sterilized are located, the sterilizing agent being in vapor or possibly liquid form, the agent heated to a temperature suitable for the procedure, namely a temperature which is lower than the temperature in the chamber, in order to avoid condensation. In other words, the sterilization or disinfection is carried out in a vacuum, whereby part of the sterilizing or disinfecting agent is draw off after it has been dosed or introduced into the chamber, after which it is added again in order to provide a higher concentration of active substance in the autoclave.

The procedure can be performed in a temperature range from about 20° to 60° C., preferably about 20° to 55° C., most preferably about 40° to 50° C. It is most advantageous to use a temperature of about 45° C. at which the heating stress on objects to be sterilized is insignificant.

Vaporization can be performed with means disposed in the chamber itself, or outside of the chamber. In practice, e.g. about 10 to 300 ml, advantageously about 30 to 100 ml. sterilizing agent per 100 liter of chamber volume, is produced to be vaporized, whereby it evaporates, fills the chamber volume, and exerts an oxidizing influence. Thereafter, the agent is drawn off by a pump whereby its odor disappears by salt formation and thus, e.g., peracetic acid is converted through sodium peracetate to sodium acetate.

Regarding the present invention, an appropriate amount of the sterilizing agent of the invention is about 1 to 100 mg per liter of chamber volume, preferably about 10 to 100 mg per liter of chamber volume. For example, a 20 to 50% by weight aqueous peracid solution is used for sterilizing agent. If well over a 50% concentration is used, then the agent might be explosive.

BRIEF DESCRIPTION OF THE DRAWING

The present invention will be described below in greater detail with reference to a preferred embodiment which is illustrated in the accompanying drawing, and to which the present invention is not however restricted in any way to the specific details thereof.

The FIGURE is a schematic illustration of means and procedure for performing the present invention.

DESCRIPTION OF THE PREFERRED EMBODIMENTS

An autoclave in which sterilization is performed is generally indicated by reference numeral 1. The autoclave 1 can be closed tightly with a door or a hatch 16, and is heated to a desired temperature, e.g., with a hot water jacket 19 controlled by a thermostat and connected to the outside of the autoclave 1 which is about 47° C. The warm water jacket 19 provided on the chamber 1 may also be replaced with an electrical resistance instead. Water, e.g. a spent liquid, is heated with the aid of a heating source 10 disposed in a heating vessel 3. The heating element 10 may be an electrical resistance. Continuous water circulation is provided along a water circulation system 2 comprising a pump 13 as illustrated in the FIGURE. An expansion tank 12 is also provided at the heating vessel 3 and is connected thereto. The autoclave 1 is connected to a thermometer 11, and also possibly to a pressure meter. The circulating liquid may be another liquid instead of water.

A vacuum pump 4 is connected to the autoclave 1 so that a gaseous sterilizing agent is conducted along a line 18 and through an alkalizing agent placed in a tank 17 as illustrated. Sodium hydroxide or potassium hydroxide is used for such an alkalizing agent. In this way, problems related to odor and corrosion are avoided.

A vaporizer 5 is disposed separately from the chamber 1 and is connected to the autoclave 1 through a line 14 having a valve 9 as illustrated. With a measurement vessel 6, an accurate dosing of the sterilizing agent is obtained.

The vaporization is carried with the aid of either a spiral 7 or a bowl/cup-like shaped depression at a bottom of the vaporizer 5, provided with an outlet tap 20 whereby vaporization residue following the sterilizing is removed. The draining vessel 20 for the vaporization residue is provided at the lowest point of the cup/bowl-like depression.

The sterilizing agent is heated in the vaporizer 5° to about 45° C. through a heat source 8. The temperature of the gases in the vaporizer 5 is thereby lower than in the autoclave 1. The sterilizing agent is so heated that it becomes vaporized but does not boil.

Sterilization is carried out so that the sterilizing agent present in the autoclave 1 is conducted into the autoclave 1 through the line 14 and the valve 9. The duration of the sterilization is, e.g., about 1 hour. When the sterilizing phase is over, the valve 9 is then closed. The gas used for sterilizing is pumped off as described above, and with the aid of a sterilizing filter 15 the autoclave 1 is flushed with air.

The degree of sterilization attained with the method according to the present invention and the apparatus described above is consistent with the standards which ar required for surgical instruments used in hospitals.

The embodiment of the present invention described above is merely one way of performing the sterilizing procedure of the present invention. The procedure can also be accomplished without any external or internal heating. Additionally, the vaporization of the sterilizing agent can be carried out in the vaporizer 5 or in the interior of the autoclave 1 itself.

The invention will be furthermore described below, by way of the following examples:

EXAMPLES 1-10

Instruments to be sterilized were placed in a 130 liter autoclave (1-63 PES) which was closed tightly. The temperature was set to 40° C. and a vacuum was established in the system. Altogether 100 ml of vaporized peracetic acid (concentration 40%) was fed into the autoclave, and the sterilizing was allowed to continue for one hour. After the sterilizing was over, 17 ml acid had been consumed. The results are shown in the table below:

TABLE

| No. | Germ filament | Results |
|---|---|---|
| 1 | 1 | sterile |
| 2 | 1 | sterile |
| 3 | 1 | sterile |
| 4 | 1 | sterile |
| 5 | 1 | sterile |
| 6 | 1 | sterile |
| 7 | 1 | sterile |
| 8 | 1 | sterile |
| 9 | 1 | sterile |
| 10 | 1 | sterile |

The preceding description of the present invention is merely exemplary, and is not intended to limit the scope thereof in any way, so that the various details of the present invention set forth above, may vary.

What is claimed is:

1. Method for sterilizing or disinfecting instruments in a closed chamber, comprising
    carrying out said disinfecting or sterilizing with an organic peracid in a concentration of more than about 7 up to about 50% in aqueous solution, said organic peracid being a powerful oxidizing agent and wherein said disinfecting or sterilizing is additionally carried out with a quantity of agent of about 1 to 100 mg per liter of chamber volume.

2. Method for sterilizing or disinfecting instruments in a closed chamber, comprising
    carrying out said disinfecting or sterilizing with an organic peracid in a concentration of more than about 7 up to about 50% in aqueous solution, said organic peracid being a powerful oxidizing agent and wherein the concentration of said peracid in aqueous solution is about 20 to 50%.

3. The method of claim 2, wherein the concentration of said peracid in aqueous solution is about 40%.

4. Method of sterilizing or disinfecting instruments in a closed chamber, comprising
    carrying out said disinfecting or sterilizing with an organic peracid in a concentration of more than about 7 up to about 50% in aqueous solution, said organic peracid being a powerful oxidizing agent and wherein said disinfecting or sterilizing is additionally carried out at a temperature of about 20° to 60° C.

5. The method of claim 4, wherein said disinfecting or sterilizing temperature is about 20° to 55° C.

6. The method of claim 5, wherein said temperature is about 45° C.

7. Method for sterilizing or disinfecting instruments in a closed chamber, comprising
    carrying out said disinfecting or sterilizing with an organic peracid in a concentration of more than about 7 up to about 50% in aqueous solution, said organic peracid being a powerful oxidizing agent additionally comprising
    carrying out said disinfecting or sterilizing in a vacuum, and
    drawing off part of said agent after said agent has been introduced into said chamber, and
    adding said withdrawn agent back into said chamber in order to provide a higher concentration of active substance in said chamber.

8. Method for sterilizing or disinfecting instruments in a closed chamber, comprising
    carrying out said disinfecting or sterilizing with an organic peracid in a concentration of more than about 7 up to about 50% in aqueous solution, said organic peracid being a powerful oxidizing agent and wherein said disinfecting or sterilizing is carried out in a non-vacuum.

9. The method of claim 8, additionally comprising vaporizing about 10 to 300 ml of agent per 100 liter of chamber volume.

10. The method of claim 9, additionally comprising vaporizing about 30 to 100 ml of agent per liter of chamber volume.

11. Method for sterilizing or disinfecting instruments in a closed chamber, comprising
    carrying out said disinfecting or sterilizing with an organic peracid in a concentration of more than about 7 up to about 50% in aqueous solution, said organic peracid being a powerful oxidizing agent, and additionally comprising heating said agent to a suitable temperature by vaporizing.

12. The method of claim 11, wherein said vaporizing is carried out in apparatus separate from said closed chamber.

13. The method of claim 11, wherein said vaporizing is carried in said chamber itself.

* * * * *